United States Patent
Yonezawa et al.

(10) Patent No.: US 7,009,196 B2
(45) Date of Patent: Mar. 7, 2006

(54) INSPECTION APPARATUS FOR INSPECTING RESIST REMOVAL WIDTH

(75) Inventors: Eiji Yonezawa, Aichi (JP); Tadashi Aoyama, Aichi (JP)

(73) Assignee: Nidek Co., Ltd., Aichi (JP)

( * ) Notice: Subject to any disclaimer, the term of this patent is extended or adjusted under 35 U.S.C. 154(b) by 273 days.

(21) Appl. No.: 10/401,142

(22) Filed: Mar. 28, 2003

(65) Prior Publication Data

US 2003/0222231 A1    Dec. 4, 2003

(30) Foreign Application Priority Data

Mar. 28, 2002   (JP)   .......................... P2002-092260

(51) Int. Cl.
    $G01N\ 21/86$    (2006.01)
(52) U.S. Cl. ................. 250/559.24; 356/237.2
(58) Field of Classification Search .. 356/237.1–237.5; 250/559.24, 559.36; 382/145, 147–149
    See application file for complete search history.

(56) References Cited

U.S. PATENT DOCUMENTS

| 6,222,624 B1 | 4/2001 | Yonezawa | |
|---|---|---|---|
| 2003/0030050 A1 * | 2/2003 | Choi | ........................... 257/4 |

FOREIGN PATENT DOCUMENTS

| EP | 0977029 A1 | 2/2000 |
|---|---|---|
| WO | WO 02/23123 A1 * | 3/2002 |

* cited by examiner

Primary Examiner—Thanh X. Luu
(74) Attorney, Agent, or Firm—Sughrue Mion, PLLC

(57) ABSTRACT

An inspection apparatus for inspecting a resist boundary on a substrate having an outer surrounding portion, includes: an illumination unit which illuminates the outer surrounding portion of the substrate; a detector which detects light reflected from the outer surrounding portion; and a judgment unit which judges, based on light intensity of the detected reflected light, whether a resist removal width is proper.

12 Claims, 6 Drawing Sheets

INSPECTION APPARATUS FOR INSPECTING RESIST REMOVAL WIDTH

BACKGROUND OF THE INVENTION

The present invention relates to a resist removal width inspection apparatus for inspecting whether a width of resist material removed, in a photo process, from the outer surrounding part of a resist-coated semiconductor wafer, glass substrate or the like, is proper or not.

In a photo process of forming a pattern on a semiconductor wafer, a wafer is coated with a resist material, and a resist layer formed on the wafer is exposed to light through a pattern by using the photographic technique, so as to form a minute pattern on the wafer. In the process, there is possibility of generating dust particles due to contact of the resist material attached to the outer surrounding portion of the wafer with the carrier. To avoid the dust generation, after the resist coating, the resist material is removed from an outer surrounding portion over a fixed width (this width will be referred frequently to as a resist removal width) on the resist-coated wafer (edge bead removal (EBR) process). In this case, if the resist material is excessively removed, an original resist pattern is adversely affected, and if the resist removal width is narrow, dust may be generated. Accordingly, it is necessary to inspect whether the resist removal width is proper or not. Conventionally, a visual inspection is employed for inspecting the resist removal width. That is, an operator applies light to the resist-coated wafer, visually checks a color change of light reflected from the wafer, discriminates an edge (boundary position) of the resist based on the color change, and judges whether the resist removal width is proper or not, by its position and shape.

The visual inspection by the operator inevitably suffers from adverse influences of the dust generated by the operator himself or herself upon the inspection result and a variation caused by individual difference in the inspection result. Further, the inspection result is utilized for only an examination pass decision, and cannot be utilized for management based on numerical values of inspection contents. For this reason, there is a need of automatizing the inspection process of the resist removal width.

SUMMARY OF THE INVENTION

For the above background reasons, the invention has an object to provide an inspection apparatus which is capable of automatically inspecting a resist removal width of a resist material on the outer surrounding portion of a resist-coated wafer.

In order to solve the aforesaid object, the invention is characterized by having the following arrangement.

(0) An inspection apparatus for inspecting a resist boundary on a substrate having an outer surrounding portion, the inspection apparatus comprising:
an illumination unit which illuminates the outer surrounding portion of the substrate;
a detector which detects light reflected from the outer surrounding portion; and
a judgment unit which judges, based on light intensity of the detected reflected light, whether a resist removal width is proper.

(2) The inspection apparatus according to (1), wherein
the illumination unit illuminates the outer surrounding portion with a plurality of narrow band light which are different in center wavelength, and
the judgment unit judges, based on a wavelength characteristic obtained from the light intensity for each wavelength, whether the resist removal width is proper.

(3) The inspection apparatus according to (2), wherein the judgment unit obtains wavelength characteristics at two positions, one being located inwardly slightly from a tolerance range of the resist boundary and the other being located outward slightly from the tolerance range, and judges, based on comparison of the obtained wavelength characteristics and a reference wavelength characteristic, whether the resist removal width is proper.

(4) The inspection apparatus according to (1), wherein the judgment unit obtains a position of the resist boundary based on change of the light intensity in a radial direction of the substrate, and judges, based on the obtained resist boundary position, whether the resist removal width is proper.

(5) The inspection apparatus according to (4), wherein the judgment unit obtains a winding of the resist boundary based on the obtained resist boundary position, and judges, based on the obtained winding, whether the resist removal width is proper.

(6) The inspection apparatus according to (4), wherein the judgment unit judges, based on a breaking in which the resist boundary position cannot be obtained, whether the resist removal width is proper.

(7) The inspection apparatus according to (1), wherein
the substrate is a semiconductor wafer, and
the judgment unit judges, based on the light intensity at at least three portions of the outer surrounding portion of the wafer, whether the resist removal width is proper.

(8) The inspection apparatus according to (1) further comprising: a defect detecting unit which macro-inspects a defect on the substrate by processing an image formed by the light reflected from the substrate.

(9) The inspection apparatus according to (1), wherein the judgment unit judges, based on the light intensity, whether the resist boundary falls within a predetermined tolerance range on the outer surrounding portion.

(10) An inspection apparatus for inspecting a resist boundary on a substrate having an outer surrounding portion, the inspection apparatus comprising:
an illumination unit which illuminates the outer surrounding portion of the substrate;
a light detector which detects light reflected from the outer surrounding portion; and
an image processor stores program for judging, based on light intensity of the detected reflected light, whether a resist removal width is proper.

(11) The inspection apparatus according to (10), wherein
the illumination unit illuminates the outer surrounding portion with a plurality of narrow band light which are different in center wavelength, and
the program includes a program for judging, based on a wavelength characteristic obtained from the light intensity for each wavelength, whether the resist removal width is proper.

(12) The inspection apparatus according to (11), wherein the program causes the image processor to execute a step of obtaining wavelength characteristics at two positions, one being located inwardly slightly from a tolerance range of the resist boundary and the other being located outward slightly from the tolerance range, a step of comparing the obtained wavelength characteristics with a reference wavelength characteristic and a step of judging, based on the comparison of the obtained wavelength characteristics and the reference wavelength characteristic, whether the resist removal width is proper.

(13) The inspection apparatus according to (10), wherein the program causes the image processor to execute a step of obtaining a resist boundary position based on change of the light intensity in a radial direction of the substrate, and a step of judging, based on the obtained resist boundary position, whether the resist removal width is proper.

(14) The inspection apparatus according to (13), wherein the program causes the image processor to execute a step of obtaining a winding of the resist boundary based on the obtained resist boundary position, and judging, based on the obtained winding, whether the resist removal width is proper.

(15) The inspection apparatus according to (13), wherein the program causes the image processor to execute a step of judging, based on a breaking in which the resist boundary position cannot be obtained, whether the resist removal width is proper.

(16) The inspection apparatus according to (10), wherein the substrate is a semiconductor wafer, and
   the program includes a program for judging, based on the light intensity at at least three portions of the outer surrounding portion of the wafer, whether the resist removal width is proper.

(17) The inspection apparatus according to (10), wherein the program includes a program for judging, based on the light intensity, whether the resist boundary falls within a predetermined tolerance range on the outer surrounding portion.

DETAILED DESCRIPTION OF PREFERRED EMBODIMENTS

Figure 1:
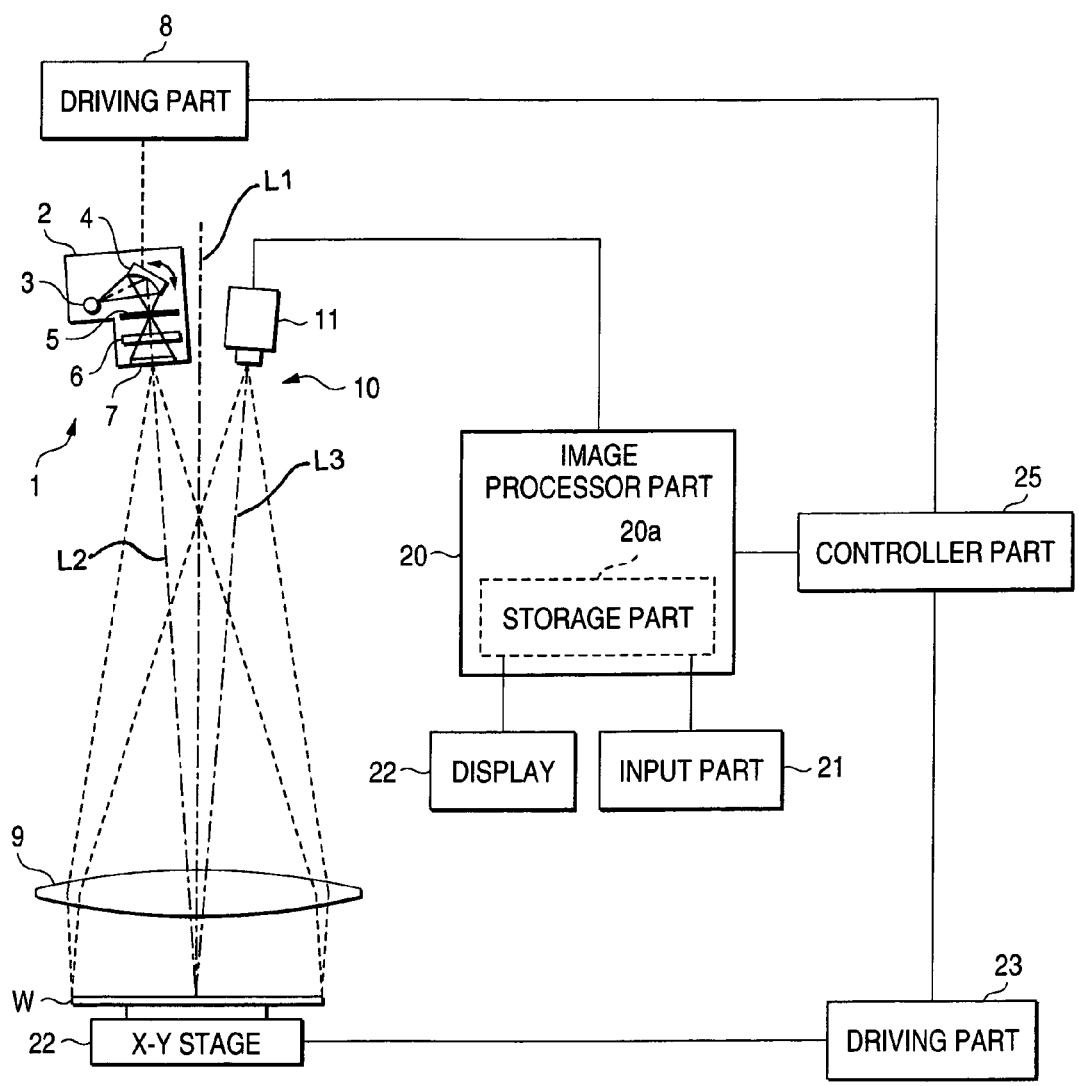
FIG. 1 is a diagram showing a schematic arrangement of an inspection apparatus constructed according to the invention.

A preferred embodiment according to the present invention will be described with reference to the accompanying drawings. FIG. 1 is a diagram showing a schematic arrangement of an inspection apparatus constructed according to the invention.

Reference numeral 1 designates an illumination optical system for illuminating a wafer W as a substrate to be inspected, which is placed on an X-Y stage 22. The illumination optical system 1 includes an illumination unit 2 and a collimator lens 9 which has a diameter larger than and a diameter of the water W. A detection optical system 10 receives light reflected from the wafer W illuminated by the illumination optical system 1, and includes the collimator lens 9, which is also used by the illumination optical system 1, and a CCD camera 11.

An optical axis L3 of the detection optical system 10 is symmetrical with an optical axis L2 of the illumination optical system 1 with respect to an optical axis L1 of the collimator lens 9. The CCD camera 11 picks up an inspection surface of the wafer W by using regular reflection light from the wafer W illuminated by the illumination optical system 1. The optical axis L2 of the illumination optical system 1 is arranged to be slanted with respect to the optical axis L1 of the collimator lens 9 so as not interfere with the illumination unit 2 and the CCD camera 11 and so as to illuminate the wafer W in a direction substantially perpendicular to the wafer W. In an alternative, the optical axis L1 of the collimator lens 9 maybe coincident with the optical axis L2 of the illumination optical system 1 to illuminate the wafer W in a vertical direction perpendicular to the wafer W. In this arrangement, the optical axis L3 of the detection optical system 10 is also coincident with it by use of a half mirror so as not interfere with the illumination unit 2 and the CCD camera 11 and so as to pick up the inspection surface of the wafer W by using the regular reflection light.

The illumination unit 2 includes a halogen lamp 3, a grating 4, an aperture 5 having a spot opening part, and light diffusion plates 6 and 7. The halogen lamp 3 emits light of a wide band having a known spectral characteristic. By varying an inclination angle of the grating 4 by means of a driving part 8, only light of a narrow band having an intended center wavelength is selected so as to be converged to the opening part of the aperture 5 and to pass therethrough, by the diffraction by the grating 4. Light having passed through the aperture 5 is diffused, by the diffusion plates 6 and 7, into diffused illuminating light being sufficiently uniform in luminance. Illuminating light emitted from the diffusion plate 7 is made substantially parallel in rays by the collimator lens 9 and then irradiated on the wafer W.

The regular reflection light from the wafer W illuminated by the illumination optical system 1 is converged by the collimator lens 9, and an image on the entire surface of the wafer W is picked up by the CCD camera 11. A video signal output from the CCD camera 11 is input to an image processor part 20. The image processor part 20 carries out predetermined processes, such as an A/D conversion process, on the video signal obtained from the CCD camera 11. Thereafter, the image processor part 20 carries out necessary pre-processes on the video signal. The pre-processes includes, for example, a noise removal process, and a process of sensitivity correction of the image pick-up elements of the CCD camera 11. The image processor part 20 acquires inspection data of the resist removal width of the wafer W, and judges whether the resist removal width is proper or not. Reference numeral 20a designates a storage part in the image processor part 20. Reference numeral 21 is an input part for inputting inspection conditions and the like, and numeral 24 is a display. A controller part 25 is connected to the image processor part 20, a driving part 23 for moving the X-Y stage 22 in X- and Y- directions, and the driving part 8 for driving the grating 4.

Next, an inspection of the resist removal width in the inspection apparatus will be described. A wafer W from which the outer surrounding resist is removed is placed on the X-Y stage 22 by using a transporting device (not shown), and disposed so as to have predetermined positional relations with respect to the illumination optical system 1 and the detection optical system 2. The controller part 25 successively changes an inclination angle of the grating 4 to illuminate the wafer W with illuminating light of different illumination wavelengths (center wavelengths). The illumination wavelength (center wavelength) is varied in sixteen different steps within a range of 470 nm to 850 nm. The image processor part 20 successively loads sixteen images of the wafer W picked up by the CCD camera 11 into the storage part 20a in synchronism with a variation of the illumination wavelength (center wavelength), which is controlled by the controller part 25.

Figure 2:
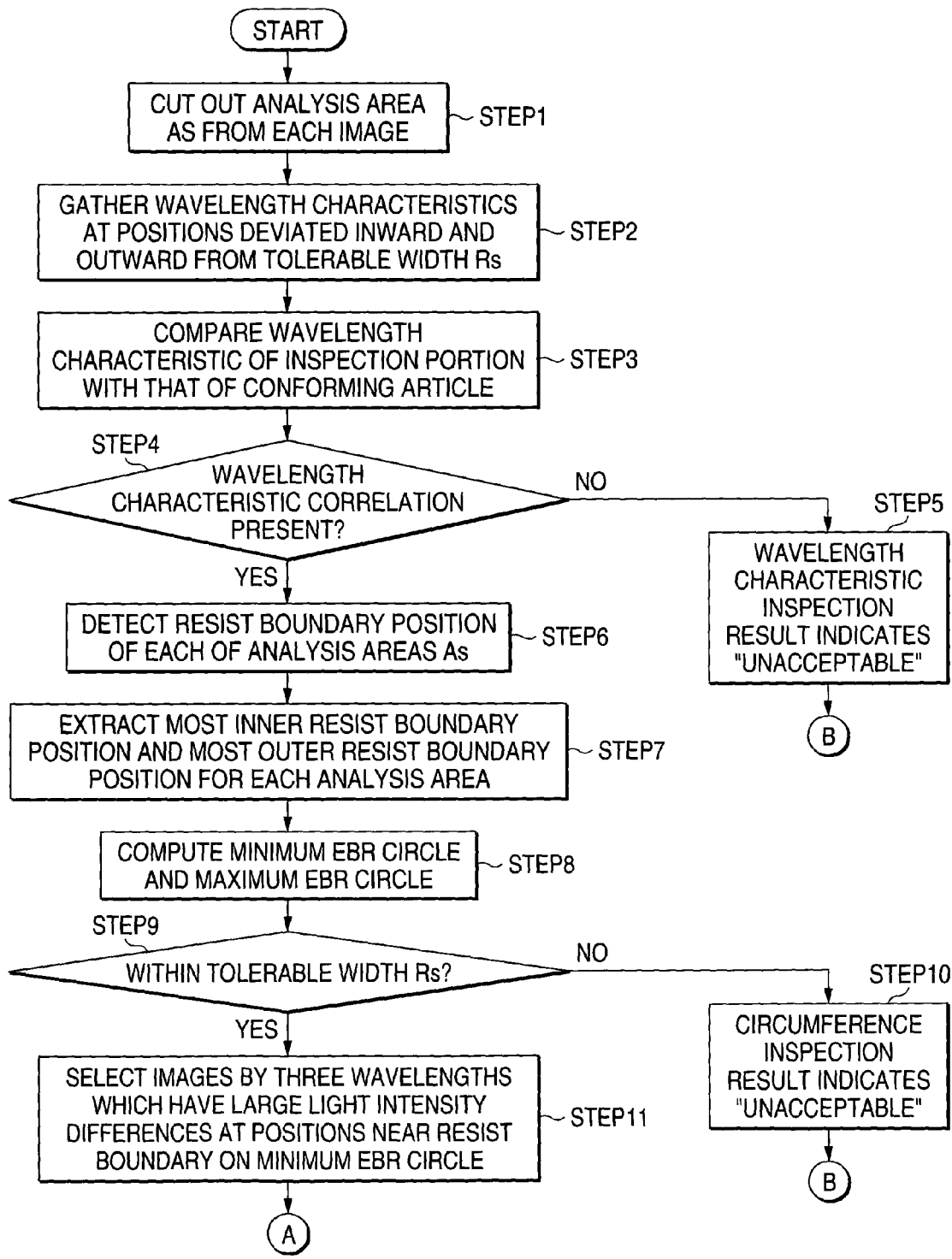
FIG. 2 is a flow chart showing procedural steps of an inspection program.
Figure 3:
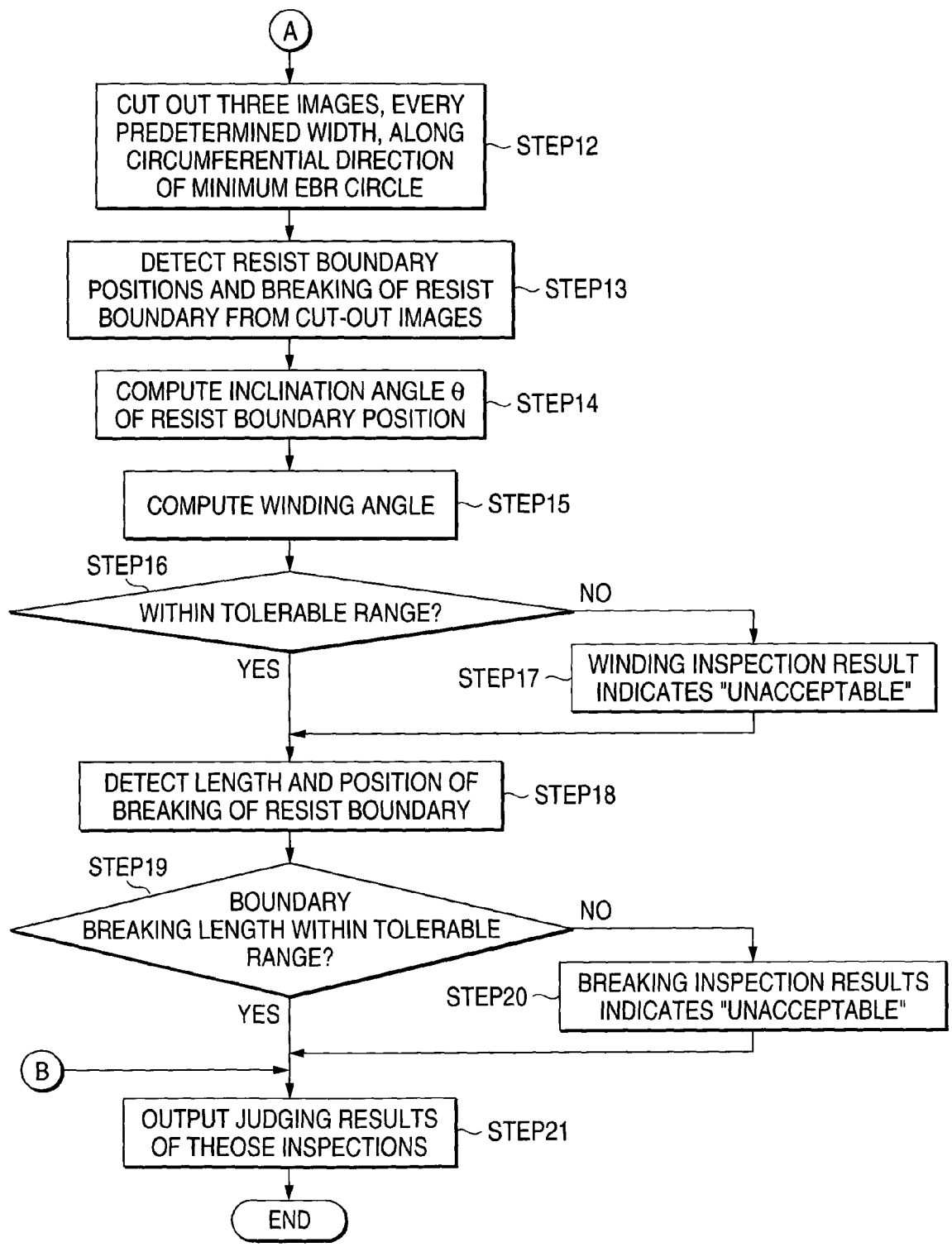
FIG. 3 is a flow chart showing procedural steps of the inspection program.
Figure 4:
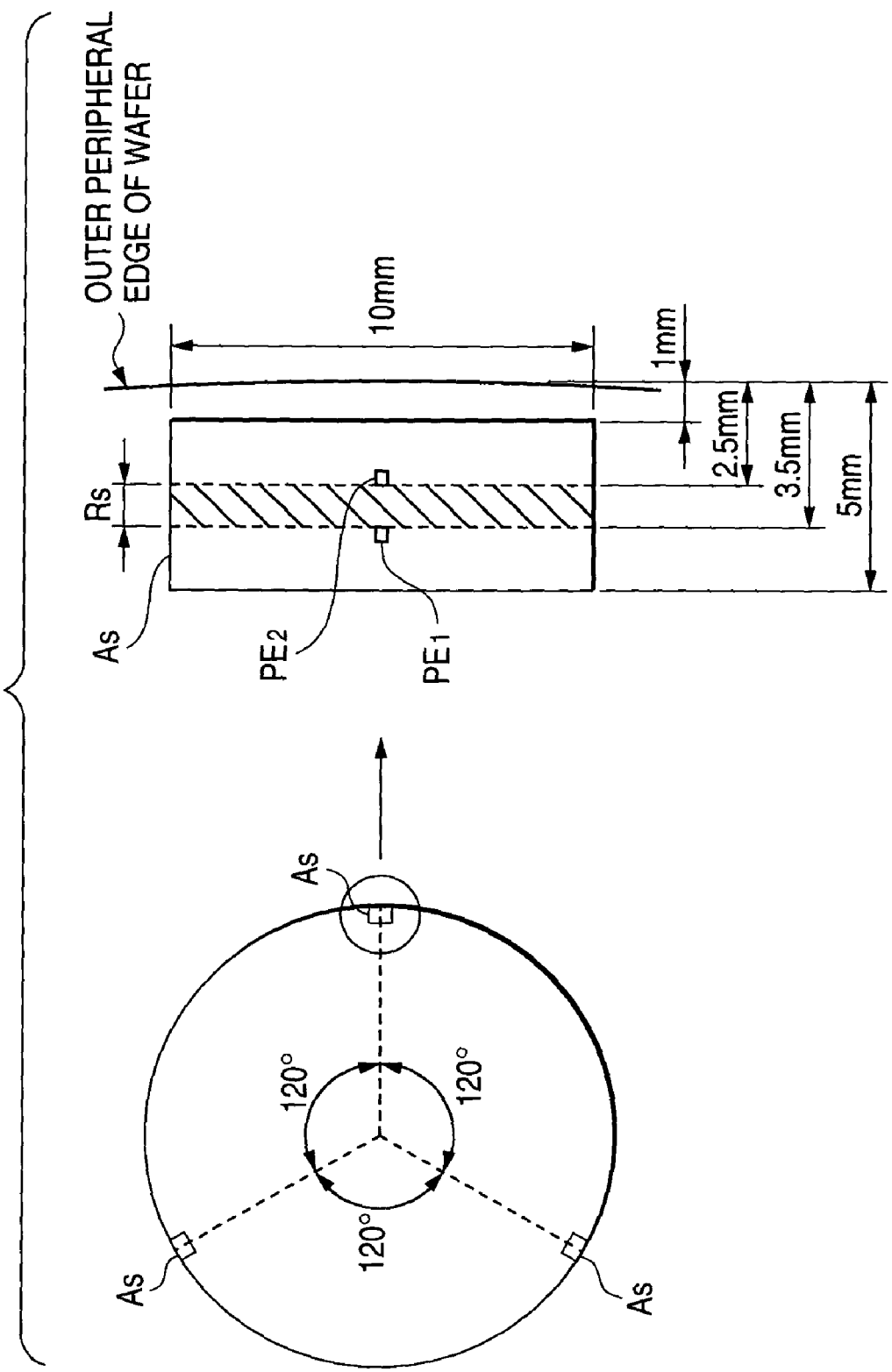
FIG. 4 is a diagram useful in explaining how to cut out an analysis area.

After completion of the loading of all of the images (sixteen images), the image processor part 20 executes an inspection program for inspecting the resist removal width. A procedure of the inspection program will be described hereunder (see flow charts of FIGS. 2 and 3). In the instant embodiment, a tolerable width Rs within which the resist boundary is to be positioned is 3.0±0.5 mm as measured from the outer peripheral edge of the wafer W (see FIG. 4).

Firstly, in an opening process, at least at three designated positions on the outer surrounding portion of the wafer W, analysis areas are cut out for each of the sixteen images picked up by varying the illumination wavelengths (step 1). The analysis areas (the tolerable width Rs) are each broader than a designated area of the resist boundary. Specifically, images are cut out at three areas As, which are angularly disposed around the wafer center at an angular interval of 120°. Each analysis area has a length of 1 to 5 mm as measured inward from the outer peripheral edge of the wafer W, and a width of 10 mm in the circumferential direction of the wafer W (see FIG. 4).

Figure 5:
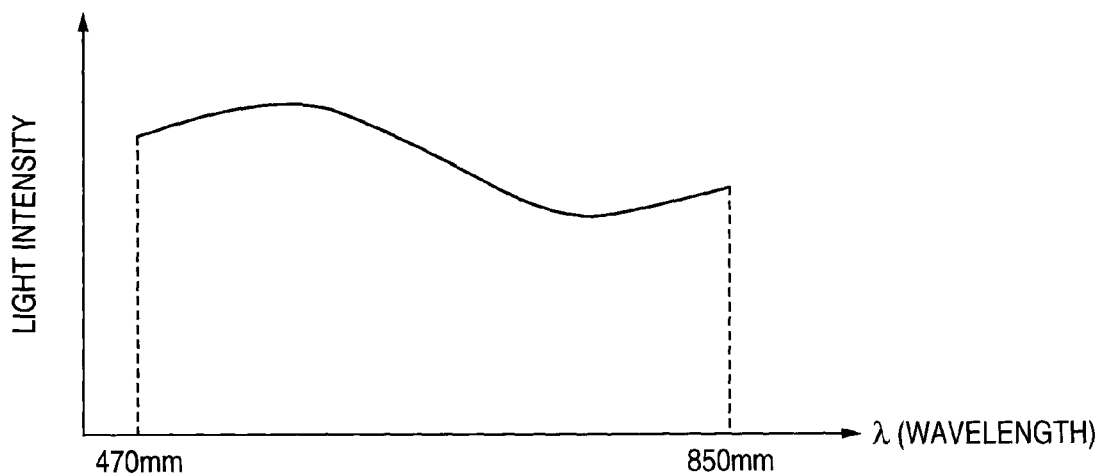
FIG. 5 is a graph showing a wavelength characteristic of one pixel position.

The images of the analysis areas As which are cut out, at three positions, from each of the sixteen images are processed to gather wavelength characteristic data of light intensity at two positions of pixels PE1 and PE2 (FIG. 4) on each of lines angularly spaced by 120°. Those pixel positions are slightly deviated inward (to the water center) and outward (to the outer peripheral edge of the wafer W) from the tolerable width Rs (step 2). FIG. 5 is a graph showing the wavelength characteristic at one pixel position. In the graph, the ordinate represents light intensity, and the abscissa represents wavelength. When the resist is present, the detected light is interference light.

Figure 6:
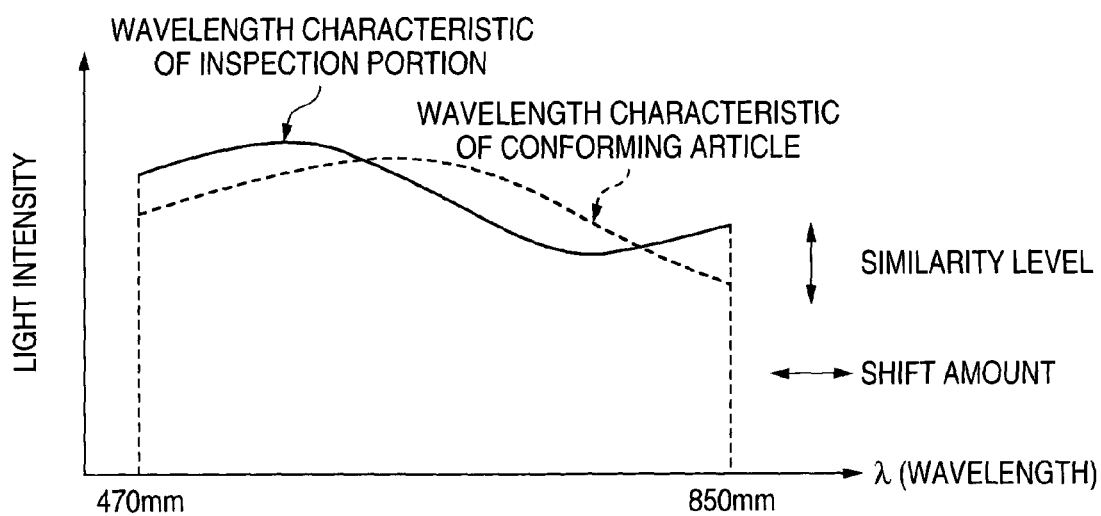
FIG. 6 is a graph comparatively showing the wavelength characteristic of an inspection portion and a conforming article.

The wavelength characteristic data at a total of six pixel positions are compared with wavelength characteristic data (reference wavelength characteristic data) of a conforming article, which are obtained in a similar way (Step 3), and a correlation between the wavelength characteristics is judged by a similarity level between them and shift amount (step S4). The similarity level is calculated as follows: light intensity difference between the wavelength characteristic data of the inspection portion (pixel position) and that of the conforming article is obtained, and an absolute value of the light intensity difference is integrated to obtain the sum of the light intensity differences, the wavelength characteristic data of the inspection portion is moved in the light intensity varying direction (ordinate) and in the wavelength direction (abscissa) with respect to the wavelength characteristic data of the conforming article to find a minimum value of the sum of the light intensity differences, and the found minimum value is determined as the similarity level. The shift amount is calculated so that a moving distance of the wavelength characteristic data of the inspection portion with respect to the wavelength characteristic data of the conforming article when the similarity level is determined as the shift amount (see FIG. 6). A one-wavelength change of the illumination wavelength is divided into a plurality of steps, and the wavelength characteristic data is moved in the wavelength direction for each step over a range of steps corresponding to two wavelengths. If the similarity level and the shift amount are out of a predetermined tolerable range, the wavelength characteristic inspection result indicates "unacceptable" (viz., the resist removal width on the wafer W is unacceptable) (step S5) If the similarity level is low, there is a possibility of trouble whether the resist is present or absent. The shift amount reflects mainly a difference between resist coating thicknesses. Accordingly, use of two different numerical values for the judgment will increase a freedom of the judgment. If no problem is found in those numerical values, it is guaranteed that the resist boundary is within the tolerable width Rs at the image cutting-out position (area).

Figure 7:
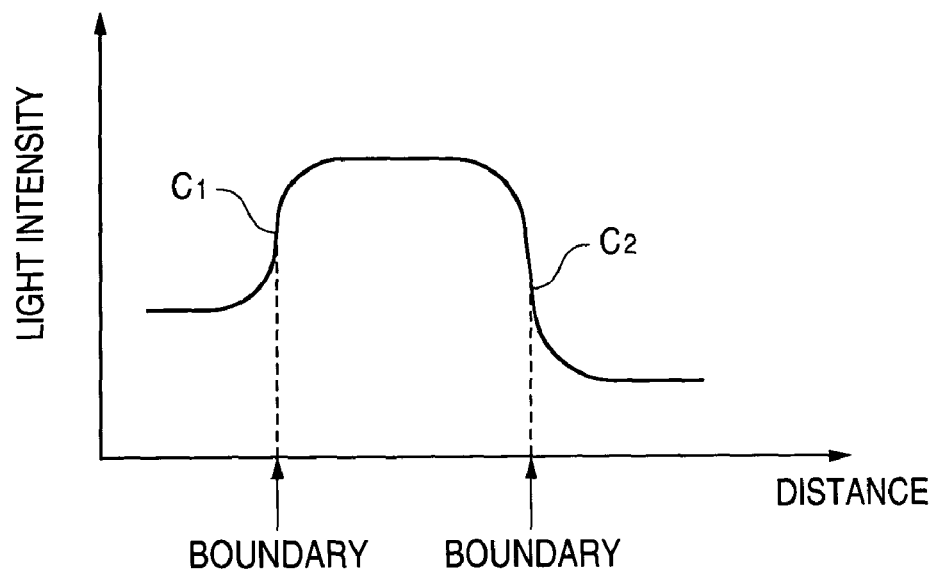
FIG. 7 is a graph showing how to detect a resist boundary position from a variation of light intensity in a radial direction.

To specify a resist removal range (width), the resist boundary position of each of the images of the analysis areas As, cut out in the step 1, is detected (step S6). In this instance, in each cut-out image, light intensities are averaged in a direction parallel to the wafer outer peripheral edge (the circumferential direction of the wafer W), and a resist boundary position is detected from a light intensity variation in a radial direction from the wafer center (see FIG. 7). Alight intensity difference is present between-the resist-coated part and the resist removal part. Therefore, a position where a variation of the light intensity is most steep is the resist boundary position. When the resist boundary in the previous step exists, plural resist boundary positions (C1 and C2 in FIG. 7) are detected. By averaging the light intensities in the direction parallel to the wafer outer peripheral edge, a component of the light intensity in the radial direction becomes small. Accordingly, only a component of the light intensity in the direction parallel to the wafer outer peripheral edge can be extracted.

Of the resist boundary positions detected in the three analysis areas As, the resist boundary position located on the most inner side (closest to the wafer center) and the resist boundary position located on the most outer side (closest to the wafer outer peripheral edge) are extracted for each of sixteen images (step S7). A minimum circle (referred to as a minimum EBR circle) passing through three points of the most inner resist boundary positions of those analysis areas As and a maximum circle (referred to as a maximum EBR circle) passing through three points of the most outer resist boundary positions are computed (step S8). An amount of deviation of each of the minimum EBR circle and the maximum EBR circle is obtained based on position data of the minimum EBR circle and the minimum EBR circle with respect to the wafer center (known coordinate point), and the position data are converted into position data relative to the wafer center. Judgment as to whether the resist removal width is proper or not is made based on whether or not the minimum EBR circle and the maximum EBR circle are each within the tolerable width Rs. When each of those circles is out of the tolerable width Rs, the circumference inspection result indicates "unacceptable" (step S10).

A winding and a breaking of the resist boundary are then inspected. The images by three wavelengths which have large light intensity differences at positions (0.25 mm) near the resist boundary, which are detected on the minimum EBR circle, are selected from the sixteen images which are picked up while varying the illumination wavelength (step S11). Three selected images of the whole wafer are cut out, every predetermined width (e.g., 0.5 mm), along the circumferential direction of the EBR circle. For the width of the cut-out image in the radial direction, if the winding of the resist boundary is actually about 0.5 mm, the image is cut out over a length of 2 mm on the minimum EBR circle. The portions on the wafer outer peripheral portion where no pattern is formed may be omitted from the area from which the image is to be cut out since the resist on those portions are removed after the pattern exposure.

The resist boundary positions on the cut-out images are detected in a manner similar to that stated above (step S13). In this case, the light intensities are not averaged in the direction parallel to the circumferential direction, and the resist boundary positions are detected every sub-pixel. When no resist boundary position is present, it is judged that the resist boundary is broken.

Figure 8:
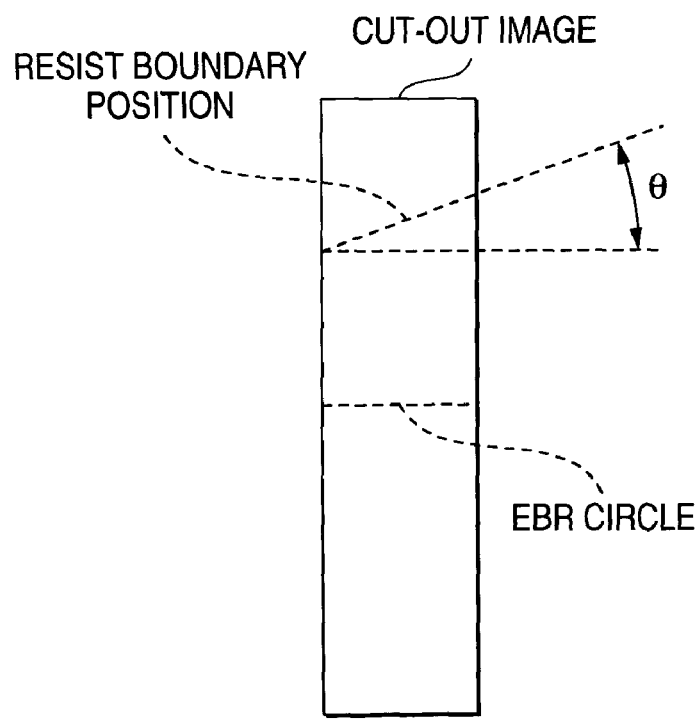
FIG. 8 is a graph showing an inclination angle θ of a resist boundary with respect to a minimum EBR circle.

For the cut-out images of which the resist boundary positions are detected, an inclination angle θ (see FIG. 8) of the resist boundary with respect to the minimum EBR circle is computed (step S14) The EBR circle and the resist boundary on each cut-out image are considered to be approximately linear. A "winding angle" is computed by totalizing and averaging the absolute values of all the inclination angles θ on the three selected images (step S15). Because of the multi-layer structure, one cut-out image possibly contains a plurality of resist boundary positions. In such a case, their inclination angles are also incorporated into the averaging. Whether a resist removal configuration is proper or not is judged from whether or not the obtained winding angle is within a predetermined tolerable range (step S16). Incidentally, in the case of the multi-layer structure, a winding angle component obtained in the previous inspection step is offset and used for the winding angle computation. If the winding angle is out of the tolerable range, the winding inspection result indicates "unacceptable" (step S17).

To detect the breaking of the resist boundary, a length and a position of a continuous resist boundary are detected (step S18). It is judged whether or not a length of a breaking of the resist boundary is within a predetermined tolerable range (step S19). To increase inspection accuracy, when two or more identical parts are found on the wafer images by different wavelengths, a maximum value of the continuous part is used for the boundary breaking length for the judgment. If the boundary breaking length is out of the tolerable range, the result of the breaking inspection indicates "unacceptable" (step S20).

After the respective inspections end, the judging results of those inspections and the numerical data used for the judgments are output (step S21). The output results are displayed on the screen of the display 24. The judging results of those inspections and the numerical data are stored in the storage part 20a and managed. Since the inspection numerical values used for the judgments of "acceptable" and "unacceptable" are obtained, it is easy to take a countermeasure in the manufacturing process for rejected articles and to take a measure for preventing defective formation.

The inspection apparatus according to the embodiment has also a function to macro-inspect repetitive patterns formed on a wafer W. The image processor part 20 image-processes the entire images (sixteen images picked up by varying the illumination wavelength) on the wafer W, which is picked up by the CCD camera 16, and detects scratch and dust, poor resist coating and various pattern defects. A repetitive pattern defect may be detected by a pattern matching process to plural images having the same positional relation of the patterns and the reference pattern. For the detail of the defect detection process, reference is made to U.S. Pat. No. 6,222,624, filed by the Assignee of the present patent application. The inspection of the resist removal width may be performed by processing the images used in the macro-inspection and in a sequence of inspection process steps. Accordingly, the inspection of high throughput is realized. The inspection apparatus for the resist removal width may be constructed as an apparatus used exclusively for the resist removal width inspection, without using the optical system and the image process of the macro-inspection apparatus.

As seen from the foregoing description, the invention successfully provides an inspection apparatus which is capable of automatizing a process for inspecting a resist removal width, and enhancing an inspection stability, and numerically managing the inspection results.

What is claimed is:

1. An inspection apparatus for inspecting a resist boundary on a substrate having an outer surrounding portion, the inspection apparatus comprising:
   an illumination unit which illuminates the outer surrounding portion of the substrate;
   a detector which detects light reflected from the outer surrounding portion; and
   a judgment unit which judges, based on light intensity of the detected reflected light, whether a resist removal width is proper,
   wherein the illumination unit illuminates the outer surrounding portion with a plurality of narrow band light which are different in center wavelength, and
   the judgment unit judges, based on a wavelength characteristic obtained from the light intensity for each wavelength, whether the resist removal width is proper.

2. The inspection apparatus according to claim 1, wherein the judgment unit obtains wavelength characteristics at two positions, one being located inwardly slightly from a tolerance range of the resist boundary and the other being located outward slightly from the tolerance range, and judges, based on comparison of the obtained wavelength characteristics and a reference wavelength characteristic, whether the resist removal width is proper.

3. The inspection apparatus according to claim 1, wherein the judgment unit judges whether the resist boundary falls within a predetermined tolerance range on the outer surrounding portion.

4. An inspection apparatus for inspecting a resist boundary on a substrate having an outer surrounding portion, the inspection apparatus comprising:
   an illumination unit which illuminates the outer surrounding portion of the substrate;
   a detector which detects light reflected from the outer surrounding portion; and
   a judgment unit which judges, based on light intensity of the detected reflected light, whether a resist removal width is proper,
   wherein the judgment unit obtains a winding of the resist boundary based on an obtained resist boundary position, and judges, based on the obtained winding, whether the resist removal width is proper.

5. The inspection apparatus according to claim 4, wherein the judgment unit judges, based on a boundary breaking length, whether the resist removal width is proper.

6. The inspection apparatus according to claim 4, wherein the judgment unit judges whether the resist boundary falls within a predetermined tolerance range on the outer surrounding portion.

7. An inspection apparatus for inspecting a resist boundary on a substrate having an outer surrounding portion, the inspection apparatus comprising:
   an illumination unit which illuminates the outer surrounding portion of the substrate;

a light detector which detects light reflected from the outer surrounding portion; and an image processor that stores a program for judging, based on light intensity of the detected reflected light, whether a resist removal width is proper, wherein the illumination unit illuminates the outer surrounding portion with a plurality of narrow band light which are different in center wavelength, and the program includes a program for judging, based on a wavelength characteristic obtained from the light intensity for each wavelength, whether the resist removal width is proper.

8. The inspection apparatus according to claim 7, wherein the program causes the image processor to execute a step of obtaining wavelength characteristics at two positions, one being located inwardly slightly from a tolerance range of the resist boundary and the other being located outward slightly from the tolerance range, a step of comparing the obtained wavelength characteristics with a reference wavelength characteristic and a step of judging, based on the comparison of the obtained wavelength characteristics and the reference wavelength characteristic, whether the resist removal width is proper.

9. The inspection apparatus according to claim 7, wherein the program judges whether the resist boundary falls within a predetermined tolerance range on the outer surrounding portion.

10. An inspection apparatus for inspecting a resist boundary on a substrate having an outer surrounding portion, the inspection apparatus comprising:

an illumination unit which illuminates the outer surrounding portion of the substrate;

a light detector which detects light reflected from the outer surrounding portion; and an image processor that stores a program for judging, based on light intensity of the detected reflected light, whether a resist removal width is proper, wherein the program causes the image processor to execute a step of obtaining a winding of the resist boundary based on an obtained resist boundary position, and judging, based on the obtained winding, whether the resist removal width is proper.

11. The inspection apparatus according to claim 10, wherein the program causes the image processor to execute a step of judging, based on a boundary breaking length, whether the resist removal width is proper.

12. The inspection apparatus according to claim 10, wherein the program includes a program for judging, based on the light intensity, whether the resist boundary falls within a predetermined tolerance range on the outer surrounding portion.

* * * * *